United States Patent
Armbruster et al.

(10) Patent No.: US 9,140,711 B2
(45) Date of Patent: Sep. 22, 2015

(54) DETERMINATION OF VITAMIN D METABOLITES IN DRIED BLOOD

(75) Inventors: Franz P. Armbruster, Bobenheim-Roxheim (DE); Hans J. Gron, Heppenheim (DE); Claudia Schumann, Weinheim (DE)

(73) Assignee: Immundiagnostik AG, Bensheim (DE)

( * ) Notice: Subject to any disclaimer, the term of this patent is extended or adjusted under 35 U.S.C. 154(b) by 0 days.

(21) Appl. No.: 14/110,035

(22) PCT Filed: Apr. 4, 2012

(86) PCT No.: PCT/EP2012/056204
§ 371 (c)(1),
(2), (4) Date: Nov. 25, 2013

(87) PCT Pub. No.: WO2012/136720
PCT Pub. Date: Oct. 11, 2012

(65) Prior Publication Data
US 2014/0072988 A1      Mar. 13, 2014

(30) Foreign Application Priority Data

Apr. 4, 2011   (DE) .......................... 10 2011 001 790

(51) Int. Cl.
*G01N 33/82* (2006.01)
(52) U.S. Cl.
CPC ..................................... *G01N 33/82* (2013.01)

(58) Field of Classification Search
None
See application file for complete search history.

(56) References Cited

U.S. PATENT DOCUMENTS

2005/0014211 A1    1/2005   Armbruster et al.

FOREIGN PATENT DOCUMENTS

| WO | WO 2005/116081 A2 | 12/2005 |
| WO | WO 2006/107992 A2 | 10/2006 |
| WO | WO 2008/092917 A1 | 8/2008 |

OTHER PUBLICATIONS

Yu et al. J. Viro. Methods 2007 vol. 142, p. 143-150).*

* cited by examiner

*Primary Examiner* — Jacob Cheu
(74) *Attorney, Agent, or Firm* — Dickstein Shapiro LLP

(57) ABSTRACT

Method and test kit for quantitative determination of Vitamin D metabolites in blood, wherein a predetermined amount of blood is pre-analytically immobilized on a solid sorption material. Thereby, hemolysis of the blood has no effect on the analysis of vitamin D metabolites. For quantitative analysis the dried blood spot on the sorption material is dissolved with an aqueous solvent buffer containing detergent, pH 7.0 to 10.0, and the vitamin D metabolites are eluted with a protic organic solution having a permittivity of less than 35. The eluate is analyzed for vitamin D metabolites using conventional methods.

12 Claims, 5 Drawing Sheets

Correlation after dry adsorption (three days)

Correlation after dry adsorption (seven days)

Figure 1A:
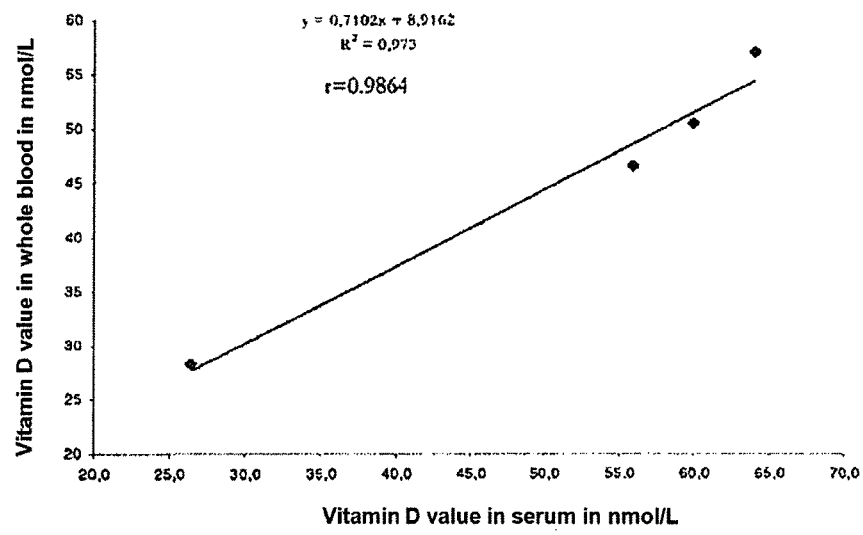
Figure 1B:
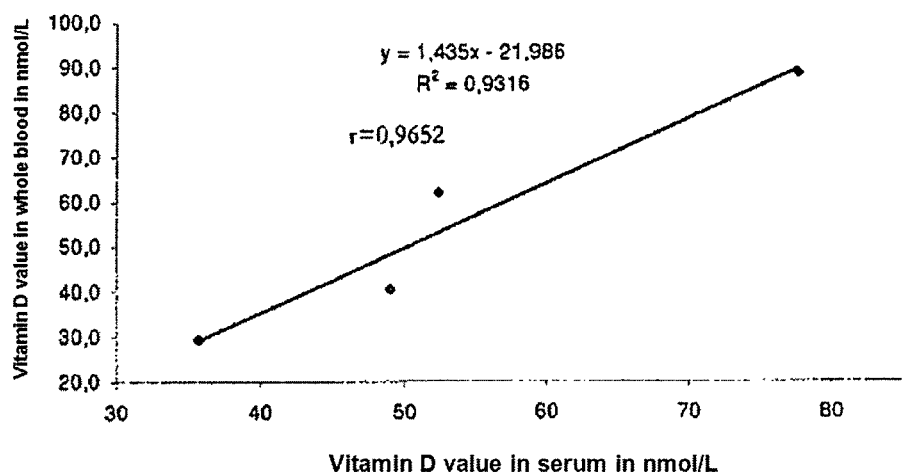
Figure 1C:
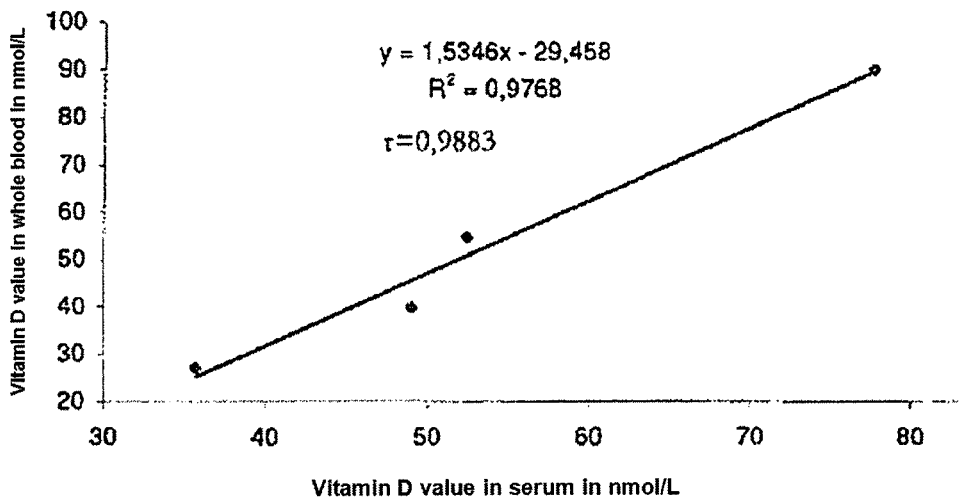
Figure 1D:
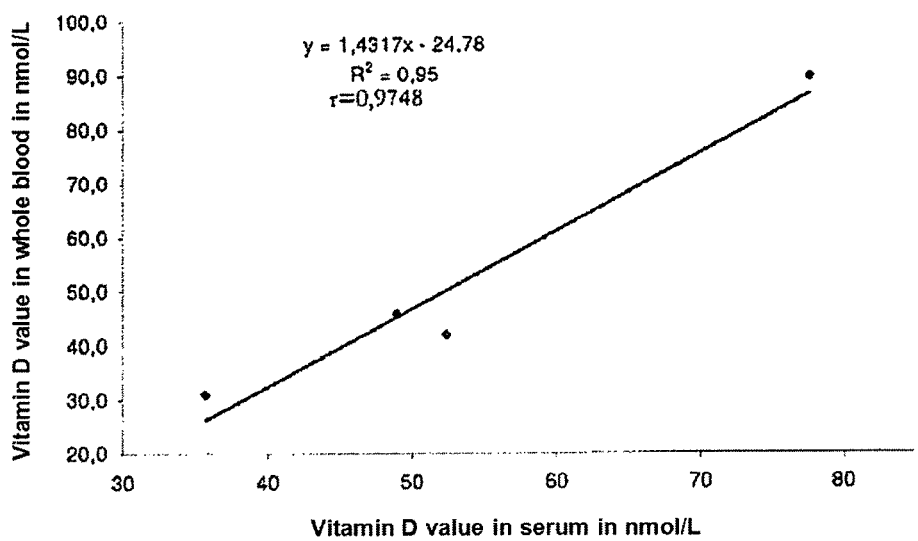

Correlation without dry adsorption upon hemolysis (state of the art)

DETERMINATION OF VITAMIN D METABOLITES IN DRIED BLOOD

FIELD OF THE INVENTION

The invention relates to methods and kits for determination of vitamin D metabolites in biological fluids, in particular in body fluids such as blood, serum or milk.

BACKGROUND OF THE INVENTION

Humans can form vitamin $D_3$ (cholecalciferol) in the skin using the UV portion contained in sunlight. Vitamin $D_2$ (ergocalciferol) is taken up from food. Ergo- and cholecalciferol differ in their side chains and biological activity. However, they are both bound by the vitamin D binding protein (VDBP) in circulation and metabolized to 25-hydroxyvitamin D (25 (OH)D or calcidiol) in the liver (see Schmidt-Gayk H, et al (ed.), *Calcium regulation hormones, vitamin D metabolites and cyclic AMP*, Springer publishing, Heidelberg (1990), pages 24-47). 25(OH)D represents the storage form in the body and is the vitamin D metabolite with the highest concentration in blood. When needed, 25(OH)D becomes hydroxylated in the kidney by 25-hydroxyvitamin D-1α-hydroxylase to 1α,25-dihydroxyvitamin D which is the D-hormone or calcitriol and the biologically active form. The activity of the vitamin D-hydroxylase is multiply regulated, e.g. by the parathyroid hormone and by the calcium level in the blood. Calcitriol is bound by the vitamin D receptor (VDR) intracellularly and transported into the nucleus where the complex with the vitamin D receptor associates to the DNA, leading to changes in protein synthesis.

Determination of vitamin D metabolites in blood or serum is medically indicated in case of suspected vitamin D deficiency, for example, due to insufficient synthesis, reduced intestinal absorption and malabsorption, liver dysfunction, increased vitamin D metabolism following the intake of antiepileptic drugs, increased loss of vitamin D in case of a nephrotic syndrome or a general disturbance of the calcium-phosphate balance. Up to one third of the elder normal population in Northern Europe are suffering for example from vitamin D deficiency when sunlight is poor during winter times (Sharla et al., Osteoporosis Int 1998; 8(2):7-12). A slight deficiency of less than 15 nanograms calcidiol per milliliter serum (37.5 nmol/L 25-OH-Vit. D/L) causes a rise in parathormone levels and increased bone resorption due to decreased calcium intake (Chapuy M C et al., J Clin Endocrinol Metab 1996, 81:1129-33). Vitamin D deficiency is therefore an important risk factor for senile osteoporosis. A severe deficiency of less than 5 nanograms calcidiol per milliliter serum (12.5 nmol/L) causes rachitis in children and osteomalacia in adults (Sharla et al., Exp Clin Endocrinol Diabetes, 1996, 104:289-292). A vitamin D deficiency is associated with a higher risk of breast, colon and prostate cancer and various autoimmune diseases such as juvenile diabetes and multiple sclerosis (Holick M F, *Vitamin D deficiency*. N Engl J Med (2007) 357:266-81). A vitamin D overdose causes the hypocalcaemia syndrome. The minimum serum concentration for bone health lies between 20 to 32 ng 25(OH)D/mL (50-80 nmol/L) and a concentration of more than 30 ng/mL or rather 75 nmol/L 25(OH)D should be sought.

The chemical methods for determination of vitamin D metabolites are laborious (see Tanner et al, J. Assoc of Analyt Chem (1988) 17, 607-710; Haddad, J G et al., J Clin Endocrinol Metab (1971) 33, 992-995 and Eisman J A et al., Anal Biochem (1977) 80, 298-305). U.S. Pat. No. 5,981,779 (Hollick et al.), WO 89/01631 and EP 0 583 945 (DeLuca et al.) teach immunological determination methods. Prior to immunological determination, samples must be carefully prepared since more than 85% of vitamin D metabolites in human serum are bound to VDBP, albumin and other proteins. WO 99/67211 (Armbruster et al.) teaches an ethanol precipitation of the serum proteins and an analysis of vitamin D metabolites in the ethanol supernatant. EP 0 753 743 (Hollis) recommends a periodate precipitation of serum proteins and an analysis of the protein-free aqueous supernatant. DE 10 144 905 C2 (Armbruster et al.) teaches an analysis directly in serum following a release of the vitamin D metabolites from their binding sites through the addition of displacement agents such as salicylic acid, warfarin or aniline sulfonic acid. WO 2002/057797 (Quest Diagnostics Inc.) claims the addition of salicylic acid, cyclodextrin and a change of pH to obtain a release of vitamin D metabolites. EP 2 126 586 B1 (Immundiagnostik AG) teaches the digestion of serum proteins by a serine protease followed by an immunoassay with a protease-insensitive monoclonal antibody. In various automated procedures, the serum sample is subjected to deproteinization and delipidation using acetonitrile. WO 2011/122948 (Future Diagnostics BV) discloses a release of vitamin D metabolites in serum samples using a fluorine-containing surfactant such as perfluorooctanoic acid.

U.S. Pat. No. 7,745,226 B2 (Clarke et al.) teaches a combination of liquid chromatography and mass spectrometry for determination of vitamin D metabolites in serum. The various LC-MS, LC-SMS and LC-TMS are hereinafter referred to as LC-MS methods (see Vogeser M, *Liquid chromatography-tandem mass spectrometry·Application in the clinical laboratory*, Clin Chem Lab Med (2003) 41:117-26; Vogeser M. Seger C. *A decade of HPLC-MS/MS in the routine clinical laboratory—goals for further developments*. Clin Biochem (2008) 41:649-62). While LC-MS analysis is considered the new standard in vitamin D analysis, there are controversies on the reliability and interpretation of the measured values because, historically, the reference values had been established by immunological methods and all therapeutic recommendations are based on them. The immunological methods usually show about 15 percent lower values than the LC-MS methods. A conversion of the values is not possible, since many of the 25(OH)D levels in serum measured by means of LC-MS in the period from 2007 to 2008 has proven as being too high (see Andrew Pollack, New York Times, 7/8 Jan. 2009). Studies using the Roche automated 25(OH)D assay show that 25-hydroxyvitamin $D_3$ in blood is stable up to 3 days at room temperature; in serum even longer (Wielders et al, Clin Chem (2009) 55(8), 1584-5). The Roche 25(OH)D assay, however, does not detect medication with vitamin $D_2$ and said studies on temperature stability of 25(OH)$D_3$ in serum do not take account of the real pre-analytical events in doctors' offices and hospitals. The 25(OH)D-EIA of Immunodiagnostic System Ltd and its automated version (Siemens ADVIA Centaur Vitamin D Total assay) are also prone to systematic errors (see Cavalier et al., JBMR (2011) 26:434-436). The current LC-MS and immunological methods may therefore lead to false measurements and to a wrong medication, in particular, when hemolysis has taken place in blood or serum samples. The prior art therefore represents a problem.

SUMMARY OF THE INVENTION

The problem is solved by the method of claim 1. Preferred embodiments of the method are disclosed in the dependent claims.

The invention relates to the pre-analytical handling of body fluid samples (blood, serum, plasma or milk) prior to a determination of the respective vitamin D metabolites and, in particular, prior a determination of the vitamin D status (total vitamin D status) comprising 25-hydroxyvitamin $D_2$, 25-hydroxyvitamin $D_3$, 1α,25-dihydroxyvitamin $D_2$, 1α,25-dihydroxyvitamin $D_3$. The invention is, however, not limited to these specific vitamin D metabolites.

The method for determination of vitamin D metabolites, individually or in combination, comprises the following pre-analytical steps: (i) provision of a solid sorption material which can physically uptake a predetermined amount of body fluid, particularly blood, wherein the sorption material is selected such that is not affected by the treatment with protic organic solvents and that does not release any analytically interfering substances; (ii) application of a predetermined amount of body fluid, for example blood, to said sorption material and adsorption of the liquid on said sorption material; (iii) storing or transporting of said sorption material with the sorbed liquid sample in protected condition until determination of vitamin D metabolites, wherein a protection against contact, moisture and/or light exposure is provided. If the invention is described as an example of whole blood, serum, plasma or capillary blood, these are preferred examples in which determination of vitamin D metabolites can be carried out. Although serum or plasma per se is not subject to haemolysis, it may still contain traces of a haemolysis, especially when the blood sample has already got old or has been handled wrongly or when it was simply prone to haemolysis.

Protection of the adsorption material against contact, moisture and light can be carried out by a wrapping, an envelope or a cassette. Preferably, the sorption material is releasable combined with the protective device and accessible for a capillary or a pipette tip via a slot or a hole. The sample sorbed on a sorption material is stable for at least seven days and longer at ambient temperature for the purposes of quantitative determination of vitamin D metabolites. Haemolysis of the blood sample on the sorption material does not interfere with the subsequent determination of vitamin D metabolites in said sample; differently to blood samples in a vessel which are "usually" subjected to haemolysis. When serum or plasma samples are prepared from haemolytic blood and subjected to a determination of vitamin D metabolites, then the measured concentrations of the vitamin D metabolites vary significantly. It is assumed that the various substances released during hemolysis react with the vitamin D metabolites in the liquid. The prior art consistently describes that even a slight haemolysis interferes. It has also been found that vitamin D metabolites are substantially temperature-stable in the pre-analytical stage when absorbed on a fibrous sorption material. Apparently, in this state—sorbed on a sorption material— they do not come in contact with catalytically active substances and, in addition, they are protected from light by the material and the wrapping. Moreover, aqueous enzymatic reactions cannot occur after adsorption on a sorption material. Without being bound to a theory, it is assumed that either proteins or enzymes responsible for an interference are found partially denatured on the sorption material or the vitamin D metabolites sorbed on the solid surface simply lack the reactants for a reaction.

The preanalytics are complemented by the following analytical steps: (i) transferring of the solid sorption material with the dried sample from the protective device into a vessel; (ii) adding of an amount of aqueous solvent buffer to the solid phase, wherein the solvent buffer has a pH between 7.0 and 10.0, contains one or more detergents and surfactants and, optionally, 0.001 to 100 mmol/L, preferably 1 to 20 mmol/L cyanide ions; (iii) treating of said solid sorption material with the sample with said aqueous buffer solvent, optionally at elevated temperature; and (iv) another adding of an amount of an organic elution solution to obtain in the vessel a liquid phase which has a permittivity between 16 to 35, preferably between 16 and 30, particularly preferred from 22 to 28, and eluting of the vitamin D metabolites from the solid phase; (v) separating of the solid phase with the adsorption material and serum and cell proteins bound and/or precipitated thereto from the liquid phase and (vi) use of an aliquot of the liquid phase with the dissolved vitamin D metabolites for the analysis.

As long as the body fluid sample or the blood sample is sorbed on the sorption material, enzymatic and chemical reactions of the vitamin D metabolites are largely prevented due to the absence of water or reactant or both; this changes with the addition of the aqueous solvent buffer because a liquid phase is then available and a potential hemolysis of the sample will have an influence. The solvent buffer should therefore prevent reactions of the vitamin D metabolites with other soluble components of the blood or keep the dissolving process short.

The dissolving buffer can contain potassium hexacyanoferrate(II), a source of cyanide ions, PSMF, detergents and surfactants such as SDS, Triton X-100®, perfluoroalkyl compounds, perfluoroalkanoic acid and conventional agents for stabilizing and preventing microbial infestation.

The aqueous phase can further contain denaturing and displacing agents for a release of vitamin D metabolites from serum proteins. Particularly preferred are salicylates and salicylic compounds, warfarin, sulfonates, toluene sulfonates, naphthalene sulfonates, anilinonaphthalene sulfonates.

In an another embodiment of the method, the liquid phase used for the releasing of vitamin D metabolites may contain a protease which digests proteins on the sorption material. This relates in particular to the digestion of proteins such as albumin, vitamin D binding protein (DBP) and vitamin D receptor (VDR), which are all known to bind vitamin D metabolites. Particularly preferred is the use of proteinase K. Proteinase K is a highly active serine protease from *Tritirachium album* which has a broad specificity for native and denatured proteins and digests also denatured proteins that are found on a hydrophobic adsorption material (Roelcke D & Uhlenbruck G, Z Med Mikrobiol Immunol (1969) 155:156-170). Denaturing agents such as sodium dodecyl sulphate (SDS) or urea as well as elevated temperatures of 50 to 60 degrees Celsius increase its activity. A concentration range from 100 µg to 2 mg/mL for the treatment of the adsorption material is recommended; a final concentration of 100 to 300 µg/mL in dissolving buffer at 37 to 50 degrees Celsius is preferred.

The pH of the dissolving buffer is preferably between 7.0 and 10.0, particularly preferred between 7.0 and 8.0. A preferred buffer for solubilisation of dried blood on the adsorption material contains 50 mmol/L $NaH_2PO_4/Na_2HPO_4$, pH 8.0, 1% gelatine, 10 mmol/L cyanide ions, 2 mmol/L EGTA, 1 mM β-mercaptoethanol, 1% SDS, 250 µg/mL proteinase K.

The aqueous phase can optionally contain up to 5 weight percent, preferably 1 to 3 weight percent native and/or chemically modified cyclodextrin to exclude interfering fatty acids, cholesterol and other lipids. Cyclodextrins can be chemically modified, for example, having groups as methyl, ethyl, propyl, hydroxy-ethyl, 2-hydroxypropyl, glycosyl, maltosyl, carboxymethyl. Native cyclodextrins and 2-hydroxypropyl-β-cyclodextrin are particularly preferred. These substances can also be included in the subsequent lipophilic elution buffer and added in increments.

Overall, short dissolving times of the sorbed sample on the solid phase are preferred. Preferably are release times from 10 to 300 seconds at a temperature from ambient temperature to 60° C., preferred from ambient temperature to 40° C.

The protic organic phase for the eluting of lipophilic vitamin D metabolites should have a permittivity ϵ less than 35, preferably less than 30. Preferred are mixtures of methanol and propanol in a volume ratio from 95 to 5 up to 5 to 95. Particularly preferred is a methanol-isopropanol mixture in a volume ratio from 80 to 20 up to 95 to 5. Other suitable protic solvent for the releasing of vitamin D metabolites from the adsorption material are propanol, butanol, isobutanol, ethylene glycol, acrylonitrile, acetonitrile, acrylic esters, dimethylacetamide, dimethyl formamide, dimethyl sulfoxide, β-keto ester, methyl ethyl ketone, N-methyl-2-pyrrolidone, N-methyl formamid, isoamyl alcohol, nitrobenzene, nitromethane, acetoacetate, perfluoroalkanoic acids, perfluorosulfonic acids, and mixtures thereof, so that the appropriate permittivity over the mixing ratio is achieved.

After elution of the vitamin D metabolites, the solid phase is removed by centrifugation and the supernatant containing the dissolved vitamin D metabolites used in the analysis. In automated methods, the solid phase is preferably filtered off from the sample and the filtrate with the dissolved vitamin D metabolites used in the analysis.

Determination of vitamin D metabolites in the supernatant or filtrate can be carried out in a competitive binding assay, preferably in a competitive binding assay based on antibodies against the vitamin D analyte. The latter is required in case proteinase K was used during the releasing of vitamin D metabolites from the solid phase. Preferred methods of said competitive binding assay are described in WO 99/067211 of the Applicant, which is incorporated herein by reference in the disclosure.

The competitive binding assay can be carried out, for example, in ELISA (enzyme-linked immune sorbens assay), RIA (radioimmunoassay), FIA (fluorescence immunoassay), LIA (luminescence immunoassay) or ILMA (immuno luminometric assay). The analyte is usually 25-hydroxyvitamin $D_2$, 25-hydroxyvitamin $D_3$, 1α,25-dihydroxyvitamin $D_2$, 1α,25-dihydroxy vitamin $D_3$ (Calcitriol) as well as vitamin $D_2$ and $D_3$. Other vitamin D metabolites such as vitamin $D_4$ and $D_5$ can also be determined.

Alternatively, determination of vitamin D metabolites in the analytical sample can be carried out by tandem mass spectrometry, wherein protonated, hydrated and/or dehydrated ions of the vitamin D metabolites in the analytical sample are generated and the detection of fragments thereof for the presence and amount of vitamin D metabolites in the sample takes place. An elution of dried blood spots during sample preparation in tandem MS analysis is known in the prior art (Chase D H et al., Clin Chem (1993) 39:66-71). Hereby is, however, only a qualitative analysis of soluble amino acids possible. The quantitative determination of lipophilic vitamin D metabolites from dried blood spots was not known in the prior art.

Another aspect of the invention relates to a test kit for the pre-analytical part of the method for quantitative determination of vitamin D metabolites in blood, comprising a capillary tube for the taking and applying of a defined amount of blood sample on an adsorption material; as well as a protective device such as an envelope or a cassette containing, in a protected state, a sorption material that is so absorbent that the amount of liquid sample is effectively bound; that, besides, is not affected by protic organic solvents at subsequent treatment, does not release any analytically interfering substances and provides interactions on its surface for binding of proteins to the sorption material, wherein the sorption material is detachably connected to the envelope or cassette and can be wetted by the capillary. This kit is especially intended for the sampling of blood from fingertips, ear or other common tapping points. The kit allows eased routine diagnostics, for example for non-medical practitioners and small doctor's offices, since the transport of collected samples can be facilitated.

The analytical method of the invention offers a measuring advantage over previous methods so that, after elution of the vitamin D metabolite—without changing the medium—, the interfering proteins can directly be removed together with the sorption material from the analytical sample by centrifugation or filtration. Furthermore, a determination can be carried out directly from whole blood or capillary blood. Hemolysis on the sorption material does not interfere with the subsequent determination. Moreover, there is less risk that residual amounts of vitamin D-binding proteins remain in the system, that renature upon medium change and distort the determination. In the previous methods, uncontrollable residual amounts of vitamin D binding proteins can bind the walls of the sample vessel by physisorption and be carried up so that, upon buffer change, they bind vitamin D metabolites again and distort unpredictably the measurement results. Similar applies to the hydrophobic vitamin D metabolites that can disappear from the sample by selective adsorption on the wall of the sample vessel. Besides, the vessels for blood sample harvesting are different depending on the manufacturer and can have an influence on the determination. This is for practical reproducibility of great importance but, on a regular basis, it is not taken in consideration in conventional internal and external comparisons for reproducibility. In these series of comparisons, the same sample vessels or at least sample vessels from one manufacturer are routinely used. However, one can hardly set a doctor's office to use sample vessels of a manufacturer only for determination of vitamin D metabolites. According to the invention, all cell and plasma proteins are bound pre-analytically on one and the same tested sorption material. The problem of uncontrolled binding on the walls of the various blood harvesting vessels does not apply. Thereby, an error source is pre-analytically eliminated that remains, otherwise, in the case of all other methods. Alongside, the advantage of a safe sample handling which tolerates long transport routes is also offered.

Further advantages, features and embodiments of the invention can be taken from the detailed description of the invention, the examples and the figures.

SHORT DESCRIPTION OF THE FIGURES

Figure 2:
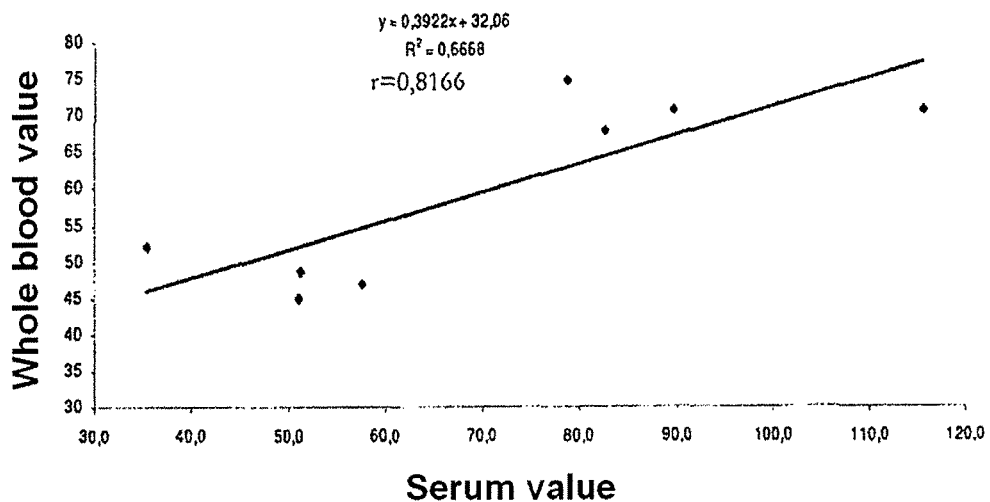
Figure 3A:
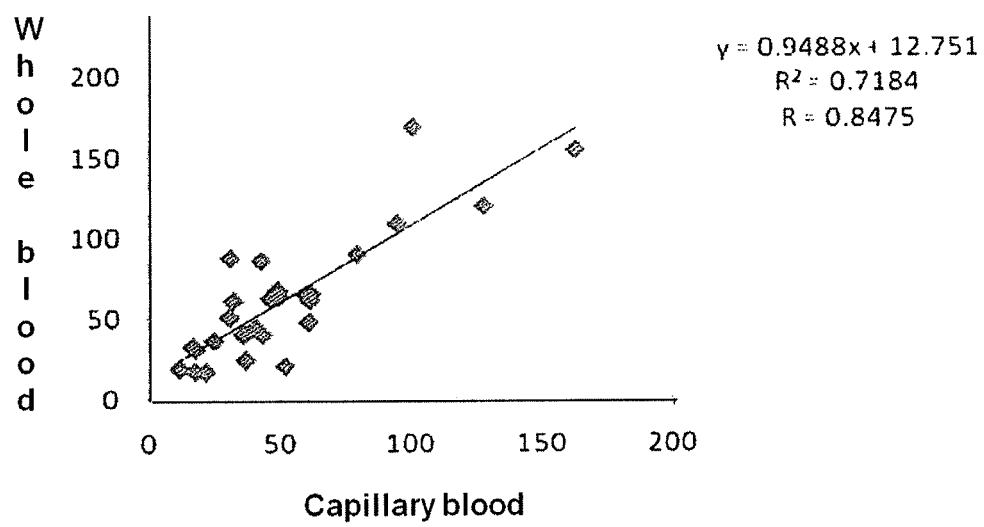
Figure 3B:
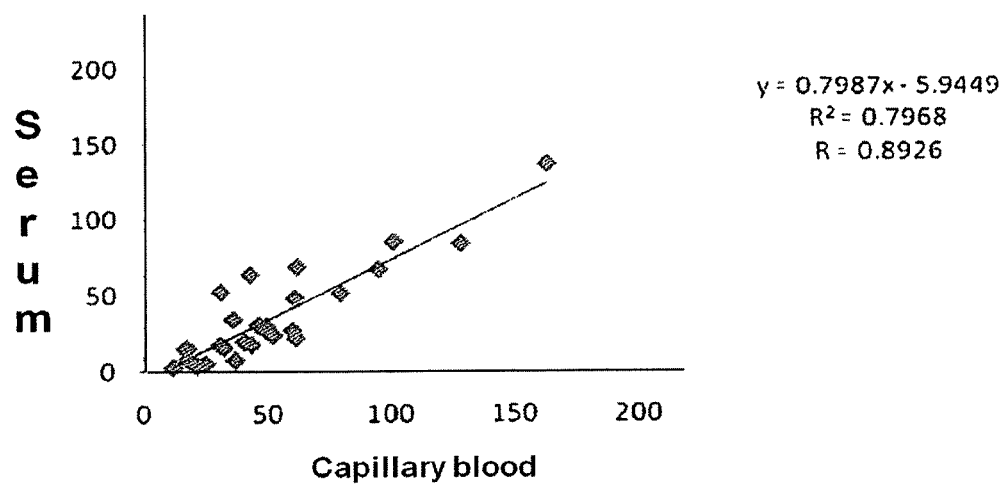
Figure 3C:
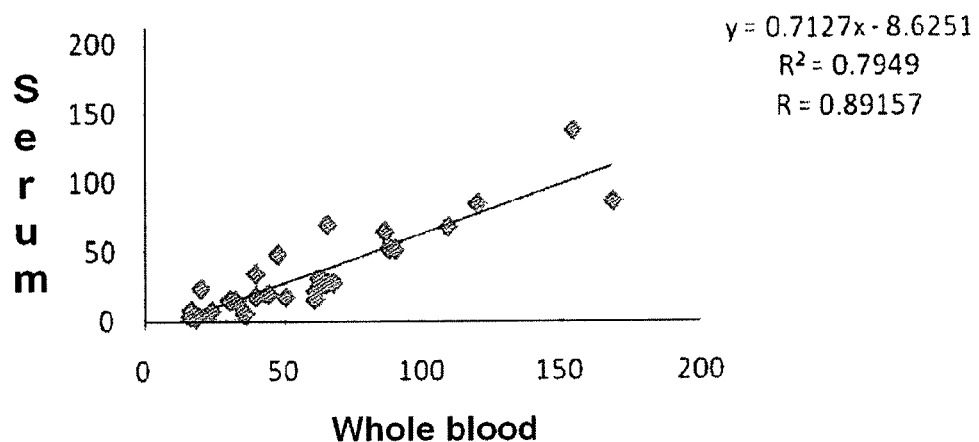
Figure 4:
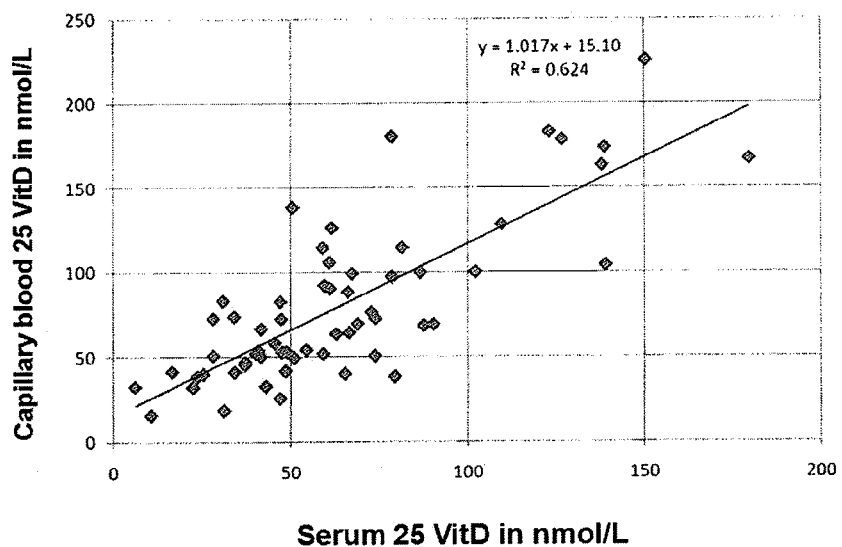

FIG. 1A-D are diagrams with graphical representations of the correlation of measured 25(OH)D concentrations in serum and whole blood after various dry adsorption times (1, 2, 3 and 7 days) on a sorption material according to the invention;

FIG. 2 is a diagram with a graphical representation of the correlation of measured 25(OH)D concentrations in serum or whole blood after hemolysis and ethanolic precipitation of serum proteins according to the prior art;

FIG. 3A-C are diagrams with graphical representations of the correlation of measured 25(OH)D concentrations in capillary blood (blood from the fingertip), EDTA-whole blood and serum (venous blood from the elbow) after various dry adsorption times on a sorption material according to the invention;

FIG. 4 is a diagram with a graphical representation of the correlation of measured 25(OH)D concentrations in capillary blood (blood from the fingertip) after short adsorption time on an sorption material and, in parallel and at the same time, determined in freshly obtained serum (venous blood from the elbow).

DETAILED DESCRIPTION OF THE INVENTION

The amount of blood applied onto the sorption material in the preanalytical stage must be measured accurately for a quantitative determination of vitamin D metabolites in said dried blood sample. This can be done with a calibrated capillary. Sample amount and sorption material amount correspond. A suitable ratio is 50 to 100 μL of blood sample on 200 to 400 μL of sorption material while other ratios are also, possible. After applying of the liquid sample onto the sorption material at ambient temperature (0 to 40 degrees Celsius), the vitamin D metabolites (and light protection) are stable. For this purpose, the sorption material is preferably placed in a protective device, in a cassette, an envelope or in any other wrapping. The sorption material is preferably accessible through a small opening or a slot for a capillary or pipette and where the blood plasma is drawn into the interior of the wrapping through the suction of the sorption material when the sample has been applied. It is then protected against contact, moisture, dirt and light for shipping, transportation and storage.

When the vitamin D metabolites are determined from capillary blood, for example, the fingertip or earlobe is tapped and, after discarding the first drop of interstitial fluid, a defined amount of blood (55% plasma and approximately 44% erythrocytes, lymphocytes, platelets) is taken up and transferred to the sorption material using a capillary. The blood sample remains there until analysis. The sorption material is a fleece-like membrane or filter material that can bind serum proteins (for example, albumin and globulins) and cellular proteins through hydrophobic interaction. Electrolytes, low-molecular substances such as sugars, lipids, and metabolites (urea, uric acid) precipitate as salts on the material or remain adsorbed on the surface. The same applies to the blood pigments hemoglobin (HbII), oxyhemoglobin (HbII-$O_2$), hemiglobin (HbIII), carboxyhemoglobin (HbII-CO). The sorption material can be cellulose, nitrocellulose, nylon, Mylar PVDF (polyvinylidene fluoride) or a material such as that used in microbiology for western blotting. The material should be filter- or felt-like and highly absorptive. The adsorption material is preferably liquid-impermeable.

The use of filter material from treated cellulose or nitrocellulose is preferred, particularly preferred is a filter material made of pure cellulose, nitrocellulose, nylon and/or PVDF (polyvinylidene fluoride), which is resistant to common organic solvents. Principally suitable filter materials are not affected by protic organic solvents. Particularly preferred are membrane materials that provide interactions for the binding of proteins but, at the same time, also have lipophobic properties. The point plotting of blood commences in case of whole blood typically a coagulation of blood and hemolysis. Moreover, serum and cellular proteins are then bound onto the sorption material by hydrophobic interactions.

Hemolysis is not harmful. Potential oxidized hemiglobin (HbIII) is converted into the stable HbIII-CN by the cyanide ions in the dissolving buffer. Bilirubin is insoluble in water and is transported in the blood as a bilirubin-albumin complex. It remains irreversibly on the sorption material. Residual amounts could interfere with peroxidase color formation in the immunoassay analysis. The dissolving buffer can optionally contain, in addition to detergents and a cyanide source, potassiumhexacyanoferrate(III) for the conversion of hemoglobin (II) into hemiglobin (III).

For their analysis, the vitamin D metabolites must be released and desorbed from the membrane, respectively. In this process, proteins on the sorption material can partly refold, regaining then their secondary and tertiary structure and binding the vitamin D metabolites on the membrane. Moreover, the vitamin D metabolites are not only bound by the vitamin D binding protein (VDBP), but also by serum proteins such as albumin, fetoprotein and so on, which are abundantly present in serum or on the sorption material. By means of organic elution agents, the vitamin D metabolites become desorbed from the solid phase and dissolved while the vitamin D binding proteins are largely transferred onto the solid phase or, as the case may be, onto vessel walls and other hydrophobic surfaces. This can tamper with the determination. The problem would persist even in case of a determination by LC-MS because only what is present in the sample solution can be determined by tandem mass spectrometry. In the present case, it is irrelevant whether the vitamin D binding proteins are on the sorption material or on the vessel wall since the liquid organic phase containing the vitamin D metabolites is always separated from the solid phase or alternatively transferred to another vessel for determination.

It is preferred in particular that the dissolving buffer contains salicylates and salicylic compounds or warfarin to displace the vitamin D metabolites from their protein binding pockets. The use of displacement agents such as salicylates and the transfer of the vitamin D metabolites from the adsorption material into a protic organic solvent with a permittivity less than 30, preferably less than 25, counteracts this problem since the interfering proteins are already partially denatured by their adsorption onto the membrane; on the other hand, they are denatured by the organic elution agent; and finally, they are removed together with the adsorption material from the liquid phase—without any change in phase—by centrifugation or filtration. Moreover, cholecalciferol and ergocalciferol (vitamin $D_2$ and $D_3$) and their derivatives are lipophilic compounds which can hardly be brought into an aqueous phase when bound by a sorption material. The elution agents as described solve this problem.

In a further embodiment, the method for determination of vitamin D metabolites comprises an adding of a serine protease with endo- and exoproteolytic activity in the dissolving buffer and a digesting of vitamin D binding proteins on the adsorption material and in solution.

One problem of colorimetric immunoassays is their susceptibility to failure due to bilirubin which consumes $H_2O_2$ in a concentration-dependent manner in the presence of a peroxidase, thus causing a reduced dye yield and spurious results. This problem is particularly evident in the determination of low concentration analytes. The interference of bilirubin can be reduced by adding potassium hexacyanoferrate(II) ($K_4Fe(CN)_6$) to the test reagent, aiming at concentrations of about 5 to 50 μmol/L in the assay mixture, see Naegele et al., Methods in Enzymatic Analysis (H U Bergmeyer, ed) 3rd Edition, *Verlag Chemie*, Weinheim, 1985, Volume VIII, pages 12-18). The dissolving buffer for the vitamin D metabolites on the adsorption material (not to be confused with the test reagent) can advantageously contain, in addition to a source of cyanide, potassium hexacyanoferrate(III) ($K_3Fe(CN)_6$). Potassium hexacyanoferrate(III) is reduced upon oxidation of hemoglobin to potassiumhexacyanoferrate (II) which is then responsible for bilirubin-interference suppression.

After separation of the sorption material and proteins, determination of the vitamin D metabolites can be carried out, for example, as described in WO 03/03391 of the Applicant. The analyte is usually selected from 25-hydroxyvitamin $D_2$, 25-hydroxyvitamin $D_3$, 1α,25-dihydroxyvitamin $D_2$, 1α,25-dihydroxyvitamin $D_3$. The protein binding analysis and the quantitative determination are carried out preferably by an ELISA (enzyme-linked immunosorbens assay), RIA (radioimmunoassay), FIA (fluorescence immunoassay), LIA (luminescence immunoassay), ILMA (immunoluminometric assay) or ECLA (electrochemical luminescence immunoassay).

The protic organic phase with the eluted vitamin D metabolites can also be analyzed by tandem mass spectroscopy after addition of deuterated vitamin D metabolite as standard. The analysis is in such a case usually preceded by a time- and labor-intensive liquid-liquid extraction or a manual solid-phase extraction (SPE) for protein removal. This form of sample preparation can be omitted. A simple trap-column prior to the analytical column is usually sufficient. The ionization of protonated, hydrated and/or dehydrated precursor ions can be carried out by APCI (atmospheric pressure chemical ionization) or ESI (electrospray ionization). Other possible ionization methods comprise photoionization, electron ionization, FAB (fast atom bombardment), LSIMS (liquid secondary ionization), MALDI (matrix assisted laser desorption ionization), field ionization and the like. The analytical column may be a conventional HPLC (high performance liquid chromatography). The determination of vitamin D metabolites from the prepared sample can then occur in many ways, compare Tsugawa et al., *Determination of 25-hydroxyvitamin D in Human Plasma Using HPLC-tandem mass spectrometry*, Analytical Chemistry (2005), 77:3001-3007, Watson D et al., *Analysis of Vitamin D and its Metabolites Using Thermospray Liquid Chromatography-Mass spectrometry*, Biomedical Chromatography (1991) 5:153-160; Kissmeyer A M et al., *Sensitive analysis of alpha,25-dihydroxyvitamin D3 in biological fluids by liquid chromatography-tandem mass spectrometry*, "J Chrome, (2001) 935:93-103; Maunsell et al., *Routine isotope-dilution liquid chromatography-tandem mass spectrometry assay for simultaneous measurement of the 25-hydroxy metabolites of vitamins D2 and D3*, Clin Chem (2005) 51:1683-1690; Yeung et al., *Characterization of the metabolic pathway of 1,25-dihydroxy-16-ene vitamin D3 in rat kidney by on-line high performance liquid chromatography-electrospray tandem mass spectrometry*, Biochem. Pharmac (1995) 49:1099-1110; Higashi et al., *Simultaneous determination of 25-hydroxyvitamin D2 and 25-hydroxyvitamin D3 in human plasma by liquid chromatography-tandem mass spectrometry employing derivatization with a Cookson-type reagent*, Biol. Pharm. Bull. (2001) 24:738-743; Odrozywolska et al., *Convergent synthesis, chiral HPLC, and vitamin D receptor affinity of analogs of 1,25-dihydroxycholecalciferol*, Chirality (1999) 11:249-255.

EXAMPLES

Example 1

Determination of Vitamin D Status in Capillary Blood (i) Pre-Analytics

Calibrated capillary tubes and bibulous adsorption material (chromatography-grade blotting filter paper with PVDF membrane from Millipore, Billerica, Mass., USA) were provided and transferred thereon a 50 μL sample of blood from finger. The first drop of interstitial fluid after tapping was discarded. The vitamin D status in circulation was used for comparison. 50 μL of capillary blood was transferred and dried on 200 μL of hydrophobic membrane material. The membrane material was encased in an envelope and thus protected from light, contact and moisture. The blood sample could be stored in this way without any change or transported at ambient temperature for 7 days and longer.

The membrane material with the dried blood spot was transferred into a 1.5 mL Eppendorf tube. This was followed by (i) 10 minute solubilising of the dried blood with 100 μL dissolving buffer (50 mM Na/K phosphate buffer, pH 8.0, 10 mM NaCl, 0.1% SDS, 100 mM sodium salicylate, 5 mM KCN) at 37° C. and by (ii) the addition of 400 μL of methanol-isopropanol mixture (7:3) to elute lipid-soluble vitamin D metabolites at ambient temperature under agitation for 30 minutes. Hemolysis did not interfere. In case of highly lipaemic samples, 2.5 weight percent of beta-cyclodextrin was added to the elution buffer to increase the reproducibility of the binding assay. The membrane material was centrifuged for 10 minutes at 3000 G; the pellet with the membrane material and precipitated denatured protein was discarded. Thereafter, the supernatant was cooled to 4 to 8 degrees Celsius and used in the analysis or frozen at −20 degrees Celsius until determination. A repeated freezing and thawing of the sample was avoided.

(ii) Analysis of 25-Hydroxyvitamin D

The quantitative determination of 25(OH)D was carried out, unless otherwise specified, strictly in accordance with the manufacturer's manual (Immundiagnostik AG, Bensheim) for quantitative determination of 25(OH)D in human serum.

For producing a streptavidin-coated microtiter plates, in each well of a microtiter plate was placed 100 ng of streptavidin dissolved in 200 μL of 60 mmol sodium bicarbonate pH 9.6 and then incubated over night at 4° C. The streptavidin solution was removed and the wells washed five times with 200 μL of washing buffer (50 mM phosphate buffer pH 6.0, 0.05% Tween-20). 250 μL of blocking buffer (phosphate buffer pH 8.0 with 0.5% casein, 1% gelatine, 1% thimerosal) were then added into each well, then incubated at room temperature for 1 hour, the blocking buffer removed and each well washed again five times with 200 μL of washing buffer. 10 ng of biotin-25(OH)D tracer (25-OH-Vit $D_3$ 3β-3'[6-N-(biotinyl)hexamido]amido-propylether; WO 99/067211 A1) in 200 μL of washing buffer were added to each well, incubated in the dark at room temperature for 1 hour and under shaking, the 25(OH)D-tracer solution was removed from the wells and each well washed five times with 200 μL of washing buffer. This was followed by a binding of largely proteinase K-resistant mouse monoclonal antibodies in liquid phase to 25(OH)$D_2$/$D_3$ in the presence of 25(OH)D from standard or analytical sample (in elution buffer).

More precisely, 40 μL of sample (analytical sample or standard) were diluted with 360 μL of assay buffer (50 mM K/Na phosphate buffer, pH 8.0, 2 mM KCl, 10 mM NaCl, 2% by weight PEG-5000, 1% gelatine) and 200 μL added to each well of a streptavidin-coated microtiter plate for the competitive binding analysis. The mixture in the well of the microtiter plate was then incubated for 3 hours at 4° C. in the dark under agitation. The 25(OH)$D_2$/$D_3$ present in the sample competed with the biotin-25(OH)$D_3$ tracer for the binding site on the antibody while said tracer-antibody complex is being desorbed from the solid phase and becoming dissolved in the solution. The assay solution was then removed from the wells and each well washed five times with 200 μL of washing buffer (50 mM K/Na phosphate buffer, pH 8.0, 2 mM KCl, 10 mM NaCl, 1% Triton X-100®).

For determination of the competitive binding, 200 μL of antibody-conjugate (peroxidase-rabbit anti-mouse mAb-conjugate) were added into the well and incubated in the dark at room temperature and under agitation for 30 minutes. The solution was removed and the wells washed five times with 200 μL of washing buffer. 100 μL of tetramethylbenzidine (TMB) substrate solution (NOVUM Diagnostika, Dietzenbach, Del.) were added into the wells for the color reaction. The color development was stopped after 30 minutes by adding 50 μL of 2 M $H_2SO_4$ in each well.

25(OH)$D_3$-assay buffer solutions of following concentrations 0, 6.4, 16, 40, 100 and 250 nmol/L were used as standards (see calibration curve). Serum and blood samples from a norm group with known 25(OH)D concentrations, determined previously, were used as controls (Ka=29.0 nmol 25(OH)D/L, Kb=75.0 nmol 25(OH)D/L). The optical density as a mean of two measurements at 450 nm is plotted on the ordinate of the diagrams with the calibration curves; the abscissa gives the 25(OH)D nmol/L concentration as determined.

Example 2

Reproducibility and Stability of the Dried Blood Sample

When dried blood samples are sent by mail or courier to the laboratory, the samples must yield the same values for the vitamin D metabolites in the respective test system after different time periods. The shipping of laboratory samples by mail or courier usually lasts no longer than seven days since the doctor and patient expect, no later than that, an early result.

50 μL-dried blood samples on 200 μL of membrane material, each prepared in accordance with example 1, were stored at ambient temperature for different periods of time (1 to 7 days). The whole dried blood samples on the membrane material were then each dissolved in 100 μL dissolving buffer as described in example 1 and treated at 37° C. for 30 minutes with a methanol-isopropanol mixture having a permittivity of 25. This resulted in a complete release of the vitamin D metabolites from the membrane while the plasma and serum proteins became denatured, notably the vitamin D binding protein. The membrane material and the denatured plasma and serum proteins were separated by centrifugation (3000 G/10 min) and 50 μL of the supernatant used as analytical sample. The standard series (serum on membrane) were treated likewise.

The analysis of the samples for 25(OH)D was done using the test system described in example 1. The correlation value r of the measured values for 25(OH)D in serum or whole blood was 0.9864 (1.0 represents full compliance) after one day of storage of the sample on the membrane material; r=0.9652 after two days; r=0.9883 after three days; and r=0.9748 after seven days; see FIGS. 1A-D. The length of storage of the sample on the membrane material had therefore no influence on the correlation of the measured values. The coefficient of determination $R^2$ corresponds to the typical pipetting variance of a manual analysis.

Example 3 (Comparative Example)

25(OH)D Determination in Whole Blood

50 μL of standard (standard series) or serum and whole blood from the same patient were pipetted into 1.5 ml tubes. 450 μL of precipitation reagent was added to each sample in accordance with WO 99/067 211, mixed and incubated at −20° C. for 30 minutes, and followed by a centrifugation at 3000 G/4° C./10 min for a separation of the precipitate. 50 μL of supernatant (analytical sample) and 100 μL of assay buffer were transferred respectively into the wells of a prepared streptavidin-coated 96-multititer plate together with biotin-25(OH)D tracer and binding protein (anti-25(OH)D-Ab) as described in example 1 and incubated at 8° C. for 3 hours. The wells were washed five times with 200 μL of washing buffer. 200 μL of peroxidase conjugated anti-mouse IgG antibody was added, incubated for 1 hour and washed again five times. The test was then developed. Table I below compares the so produced measurement values of eight serum samples and whole blood samples.

TABLE I

Results with the comparison of serum vis-à-vis whole blood in nmol/L

|  | Serum | Whole blood |
|---|---|---|
| Sample 1 | 82.7 | 67.9 |
| Sample 2 | 51.2 | 48.7 |
| Sample 3 | 78.8 | 74.8 |
| Sample 4 | 35.4 | 52 |
| Sample 5 | 89.6 | 70.8 |
| Sample 6 | 57.6 | 46.9 |
| Sample 7 | 51.0 | 45.0 |
| Sample 8 | 115.7 | 70.8 |

The table shows that the 25(OH)D determinations mostly correlate but that some diagnostic values for samples derived from whole blood differ significantly from the values determined from serum. Sometimes, the determined concentrations in whole blood are too high by half, sometimes too low by half. In fact, the correlation value r between the measured values in serum and whole blood accounts for approximately 0.8 (see FIG. 2). Thus, the measurements cannot be used as a basis for any kind of therapy.

A determination of vitamin D metabolites in whole blood for diagnosis is not possible with the established procedures. There is something present in whole blood that, upon hemolysis of the sample, interferes in an unpredictable manner with the determination of vitamin D metabolites in the sample.

Example 4

Comparison of 25(OH)D Determinations in Capillary Blood with EDTA-Whole Blood and Serum as Well as Between Whole Blood and Serum 50 μL of capillary blood from the fingertip as well as EDTA-whole blood and serum from the elbow of 25 subjects were each transferred onto 200 μL of sorption material using a capillary and, after drying on the sorption material, determined on the following day as in example 1, paragraph (ii). The results have been summarized in FIGS. 3A-C. FIG. 1A confirms that the 25(OH)D concentration in the peripheral blood vessels of the fingertip is no different to the measured concentration in EDTA-whole blood from elbow. Capillary blood results in no other values with respect to 25(OH)D than for EDTA-whole blood. The same essentially applies to the 25(OH)D determination in serum while the obtaining of serum results produces a change in volume which needs to be accounted for. Through the obtaining of serum, a "dilution effect" is obtained which has a direct impact on the 25(OH)D concentration. The coefficient of determination $R^2$ shows that the amount of sorbed liquid is decisive for determination from dried blood. Any variation in the amount of capillary blood transferred onto the sorption material by a capillary affects the precision of the measurement.

Example 5

Comparison Series of the 25(OH)D Determination in Fresh Capillary Blood with Fresh Serum from Elbow Capillary blood from the fingertip as well as serum from the elbow was obtained from 60 subjects. 50 µL of capillary blood were applied onto an absorbent lipophobic cellulose material. Simultaneously, serum was obtained from blood of the elbow, 50 µL of serum mixed with 950 µL of precipitation reagent (see WO 99/67211) and the serum proteins precipitated.

50 µL of ethanolic supernatant from the ethanol precipitation of serum proteins were used in the immunological determination.

For determination from capillary blood, the sorption material was introduced in a 1.5 ml tube, each solubilized with 100 µL of dissolving buffer for 5 minutes and treated at 37° C. for 10 minutes with 900 µL of methanol-isopropanol mixture having a permittivity of 25. The membrane material with the bound plasma and serum proteins was separated by centrifugation and 50 µL of supernatant used in the immunological determination.

The 25(OH)D determination was carried out in both cases using the test system described in example 1. The results are shown in FIG. 4. With a value of 1.017, the correlation between the series of measurements of 25(OH)D in capillary blood and serum was almost perfect. The comparatively low precision ($R^2$) value of 0.624 was caused by a transfer of varying amounts of capillary blood onto the sorption material, as became apparent from the amounts of hemoglobin in the sample. In case of dried blood determination, it is therefore recommended to simultaneously determine the amount of hemoglobin in the blood sample to improve the normalization of the amounts. The hemolysis of capillary blood on the sorption material did not disturb the determination in any case.

The invention claimed is:

1. Method for a determination of vitamin D metabolites in a sample of body fluid whose content in vitamin D metabolites is to be determined, comprising the pre-analytical steps:
    (i) providing of a predetermined amount of a bibulous solid sorption material capable of adsorbing a sample of body fluid after application which sorption material has been selected for not becoming affected by a treatment with protic organic solvents, for not releasing any analytically interfering substances and for providing interactions for a binding of proteins on its surface;
    (ii) applying of a predetermined amount of body fluid onto the sorption material and adsorbing and drying of the liquid sample on the sorption material so that the proteins contained in the liquid sample are bound to the sorption material;
    (iii) storing or transporting of the sorption material with the sorbed liquid sample in a protective enclosure under protective conditions until quantitative determination of vitamin D metabolites, wherein protection against contact, moisture and/or light exposure is provided; and
    (iv) determining the vitamin D metabolites in the sorbed liquid sample.

2. Method for determination of vitamin D metabolites according to claim 1, wherein the step of determining the vitamin D metabolites in the sorbed liquid sample comprises the following analytical steps:
    (i) transferring of the solid sorption material with the sorbed body fluid from the protective enclosure into a vessel;
    (ii) adding of an amount of aqueous solvent buffer to the solid phase, wherein said aqueous solvent buffer has a pH between 7.0 and 10.0 and contains 0.01 to 10 weight percent of a detergent and/or surfactant;
    (iii) treating of the solid phase with the sample with said aqueous solvent buffer at a temperature from ambient temperature to 60° C. for at least 10 seconds; and
    (iv) adding of an amount of a protic organic elution solution so that the liquid phase in the vessel has a permittivity of less than 35 farads/meter, and eluting of the vitamin D metabolites in the liquid phase;
    (v) separating of the solid phase with bound and/or precipitated serum and cell proteins from the liquid phase; and
    (vi) applying of an aliquot of the liquid phase with the dissolved vitamin D metabolites in the analysis.

3. Method according to claim 2, wherein the liquid organic phase for eluting of the vitamin D metabolites has a permittivity c between 16 and 30 farads/meter.

4. Method according to claim 2, wherein the liquid phase for the transferring of vitamin D metabolites in the liquid phase contains denaturing and displacing agents selected from salicylate and salicylic compounds, warfarin, sulfonates, toluene sulfonates, naphthalene sulfonates, aniline naphthalene sulfonates.

5. Method according to claim 2, wherein the liquid phase comprises a serine protease.

6. Method according to claim 1, wherein determination of vitamin D metabolites in the analytical sample is carried out by a competitive binding analysis.

7. Method according to claim 1, wherein determination of vitamin D metabolites in the analytical sample is carried out using tandem mass spectrometry wherein protonated, hydrated and/or dehydrated ions of vitamin D metabolites are generated and followed by the detection of fragments thereof for the presence and amount of vitamin D metabolites in said samples.

8. Method according to claim 1, wherein the vitamin D metabolite to be determined is selected from 25-hydroxyvitamin $D_2$, 25-hydroxyvitamin $D_3$, 1α,25-dihydroxyvitamin $D_2$, 1α,25-dihydroxyvitamin $D_3$.

9. Method according to claim 1, wherein the protein binding is carried out using an ELISA (enzyme-linked immunosorbens assay), RIA (radioimmunoassay), FIA (fluorescence immunoassay), LIA (luminescence immunoassay) or ILMA.

10. Method according to claim 1, wherein the amount of sorbed body fluid sample is co-determined via a predetermined reference material and/or the amount of sorbed hemoglobin.

11. Method according to claim 1, wherein the body fluid comprises blood or a blood fraction.

12. Method according to claim 1, wherein determination of vitamin D metabolites in the analytical sample is carried out by a competitive binding assay based on antibodies against the vitamin D-analyte.

* * * * *